United States Patent [19]
Giovanniello et al.

[11] Patent Number: 5,955,064
[45] Date of Patent: Sep. 21, 1999

[54] ENHANCED EFFICACY STABLE ANTIPERSPIRANT ACTIVE SOLUTION AND METHOD OF MAKING SAME

[75] Inventors: Rocco Giovanniello, Port Jervis; Nelson Ayala; Jing Shen, both of Middletown; Ketan Shah, Poughkeepsie, all of N.Y.

[73] Assignee: Westwood Chemical Corporation, Middletown, N.Y.

[21] Appl. No.: 08/955,056

[22] Filed: Oct. 21, 1997

[51] Int. Cl.$^6$ .............................. A61K 7/32; A61K 7/34; A61K 7/38; C01F 7/48
[52] U.S. Cl. ........................... 424/65; 423/462; 423/465; 424/66; 424/68
[58] Field of Search .................. 424/65, 66, 68; 423/462, 465

[56] References Cited

U.S. PATENT DOCUMENTS

| | | | |
|---|---|---|---|
| 4,223,010 | 9/1980 | Rubino et al. | 424/66 |
| 5,202,115 | 4/1993 | Vincenti et al. | 424/66 |
| 5,603,912 | 2/1997 | Giovanniello et al. | 423/467 |

*Primary Examiner*—Shelley A. Dodson
*Attorney, Agent, or Firm*—Ostrolenk, Faber, Gerb & Soffen, LLP

[57] ABSTRACT

An enhanced antiperspirant active having improved stability and a process for preparing the enhanced antiperspirant active solution are disclosed, the process comprises blending an enhanced basic aluminum chlorohydrate antiperspirant active having a peak 4 content of at least 20% (Component A) with a zirconium hydroxychloride neutral amino acid complex (component B) and a conventional basic aluminum chloride (Component C), the order of addition not being critical; wherein at least 10% by weight of the total aluminum being derived from Component A and about 90% to 10% of the aluminum being derived from Component C; thereby forming a stable antiperspirant active solution of enhanced efficacy, the overall concentration of reactants in solution being about 38% to 55% by weight.

26 Claims, 8 Drawing Sheets

Comparison of Chromatographic Peak Profiles

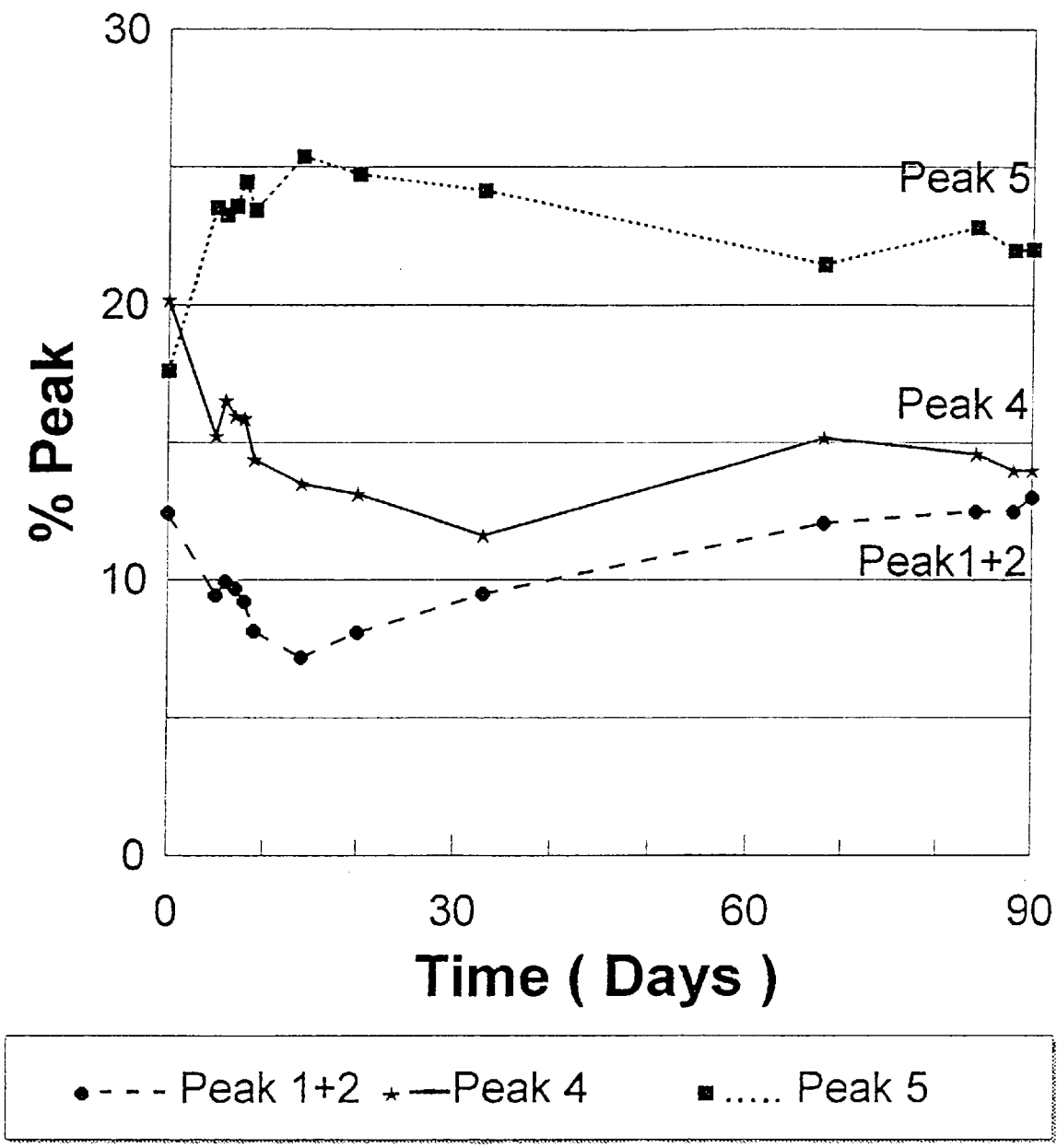
Figure 3 HPLC Polymer Stability Invention Product @ ambient Temp

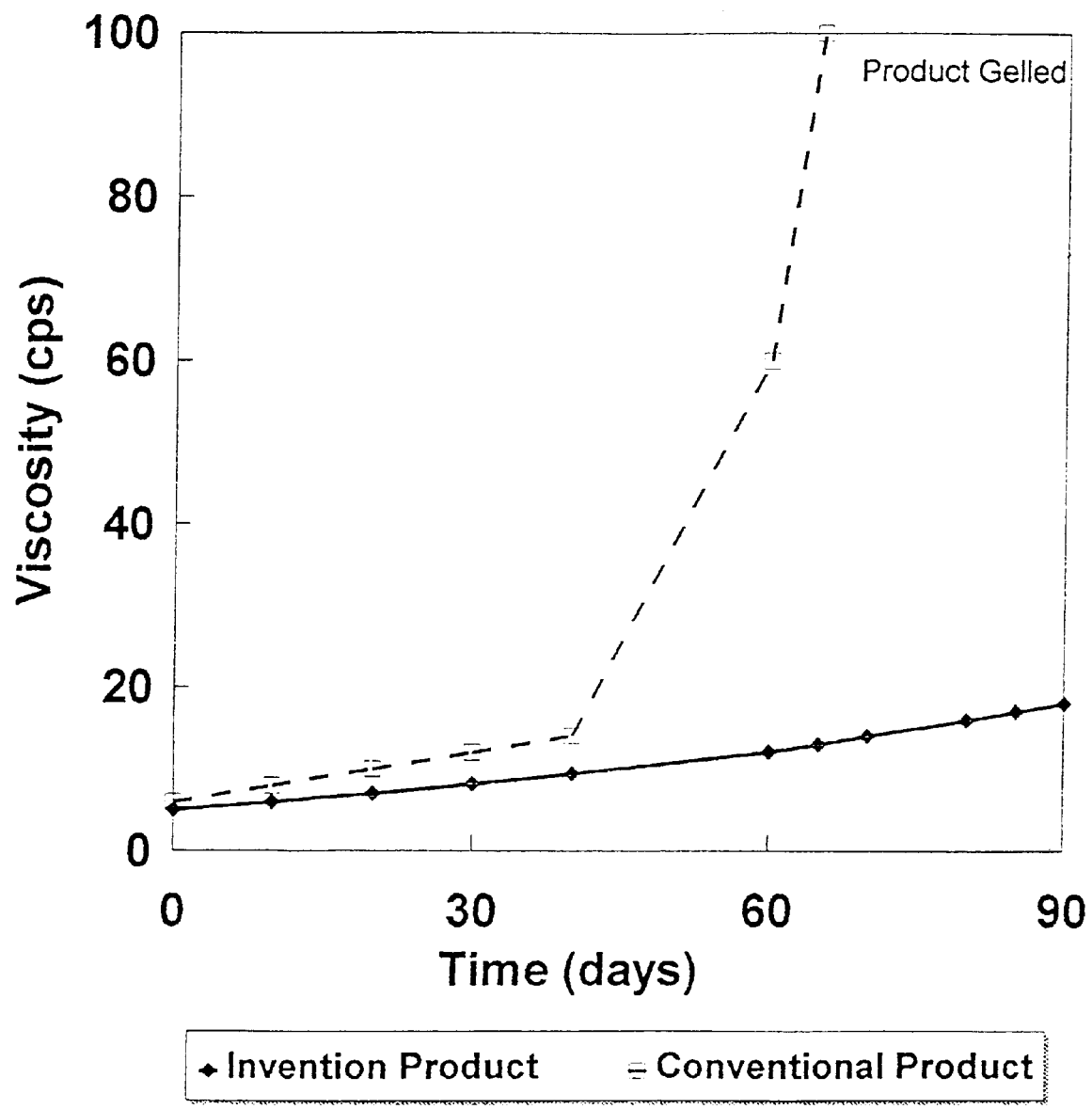

Comparison of Standard Active vs. Untreated

ENHANCED EFFICACY STABLE ANTIPERSPIRANT ACTIVE SOLUTION AND METHOD OF MAKING SAME

FIELD OF INVENTION

This invention relates to an enhanced efficacy solution of antiperspirant actives. In particular, it relates to a solution of an aluminum/zirconium complex antiperspirant active having enhanced efficacy, and polymer and viscosity stability.

BACKGROUND OF THE INVENTION

Basic aluminum halides (also referred to as aluminum halohydrates) have long been known to possess antiperspirant activity. These antiperspirant compositions are available in the form of polymeric compositions having the empirical formula:

$$Al_2(OH)_{6-y}X_y$$

wherein X is chlorine, bromine or iodine and y has a numerical value from about 0.7 to about 3. However, it is only in recent studies, as described in U.S. Pat. No. 4,359,456 (the '456 patent), that it has been shown by size exclusion chromatography that basic aluminum halides are composed of individual polymer bands which pertain to different molecular weight groups of the compound. In these studies of basic aluminum halides obtained by conventional methods of preparation it was shown that it can further be broken down from high molecular weight polymers into larger amounts of lower molecular weight polymers by diluting concentrated aqueous solutions thereof to lower aqueous concentrations and treating with heat and or aging at room temperature to produce more effective antiperspirants as shown in sweat reduction panel studies.

The '456 patent describes processes for the preparation of improved antiperspirant compositions of aluminum halohydrates, which involve heating a 2.5 to 8.5% by weight, based on aluminum, of an aqueous solution of an aluminum halohydrate of the formula:

$$Al_2(OH_{6-y})X_y$$

where X and y are as defined above, at a temperature of 50° C. to 140° C. for a period of time to impart to the aluminum product certain desired properties in respect of size exclusion chromatogram test bands. The products thus obtained from these processes have good antiperspirant activity, but the processes do not provide compositions containing larger amounts of the lower molecular weight polymers with a narrow polydispersity which are believed to possess greater antiperspirant activity.

In addition to the '456 patent, processes for the preparation of antiperspirant basic aluminum halides are shown in U.S. Pat. Nos. 3,507,896, 3,891,745, 3,904,741, 4,038,373 and 4,053,570. However, none of these patents disclose polymeric compositions possessing the desired amounts of the lower molecular weight polymers as measured by the size exclusion chromatogram test band.

U.S. Pat. Nos. 5,358,694 and 5,356,609 of Giovanniello disclose a method for preparing enhanced polymeric basic aluminum halides having the empirical formula:

$$Al_2(OH)_{6-y}X_y \cdot nH_2O$$

wherein y has a numerical value from about 0.7 to about 3; X is chlorine, bromine or iodine; n is a numeral from about 0.8 to about 4.0 and the polymer distribution as characterized by size exclusion chromatogram test is:

(a) 100% of the aluminum containing polymers are found in bands II, III and IV, and (b) band III contains at least 25% of the polymers can be prepared by reacting an aluminum metal with a halogen compound having the formula $AlX_3 \cdot H_2O$ or HX were X is as previously defined, while maintaining the temperature of the reaction mixture at about 50° C. to about 100° C. The aluminum metal is preferably in the form of pellets or powder.

The amount of water used is such as to have the final concentration of the polymer solution, in percent by weight, in the range of about 8% to about 35%, preferably about 8% to about 25%, more preferably about 15% to about 25%, and most preferably from about 17% to about 22% by weight. The reaction temperatures are preferably in the range of about 95° C. to about 100° C. Antiperspirant actives thus formed are referred to herein as "enhanced basic aluminum halides" and "enhanced basic aluminum chlorides". A fully basic form is referred to as "aluminum chlorohydrate".

Complexes of zirconium hydroxychloride and aluminum chlorhydrate are known in the art as having antiperspirant activity as disclosed in Great Britain Patent No. 2,144,992, published Mar. 20, 1985, entitled "ANTIPERSPIRANTS". The product is prepared by heating a 2–20% solution to at least 50° C. until a ratio of the heights of peaks 4 to 3 as measured by gel permeation chromatography exceeds 2:1. Complexes of the aluminum/zirconium compound with amino acids are also known in the art. While these compounds contain lower molecular weight polymers to increase efficacy they also have a wide polydispersity, a higher polymer form of aluminum to zirconium glycinate complexes and a lower cationic charge. This is evidenced from higher molecular weight polymers found in peaks (1+2) as shown in the U.K. Patent No. 2,144,992 referred to above.

U.S. Pat. Nos. 4,775,528, 5,114,705 and 5,486,347, all of which are based on the same disclosure disclose a method for preparing an enhanced Al/Zr/glycinate complex by a process which is a modification of the process disclosed in U.S. Pat. No. 4,359,456 discussed above.

Improved Al/Zr/glycinate complexes and the process for making them are disclosed in U.S. Pat. No. 4,871,525 of Giovanniello and Howe, assigned to Westwood Chemical Corporation. These compounds are prepared by first preparing a basic aluminum chloride having the empirical formula:

$$Al_2(OH)_{6-y}X_y \cdot H_2O$$

wherein y, X and n are as defined above.

The basic aluminum halide so formed is subsequently reacted with zirconium hydroxychloride and a neutral amino acid such as glycine. The aluminum chlorhydrate/zirconium hydroxyhalide complex of the '525 patent is characterized in that the peak height ratio of peak 4 to peak 3 is about 0.05 to about 1.8:1 and the peaks (1+2) content of the complex is less than 4% of the metal containing polymer distribution by weight.

The prior art, including U.S. Pat. Nos. 4,775,528, 5,114,705, 5,486,347, and 4,871,525 all disclose that solutions of the Al/Zr/glycinate complex are unstable if maintained in solution form. The method of manufacture disclosed requires rapid drying of the solution to the powder. In the alternative, the solution must be utilized without cooling while still fresh.

It is advantageous to be able to ship solutions of antiperspirant actives for direct use in aqueous based antiperspirant formulas. Avoidance of the drying step results in significant economies in production. Furthermore, where the customer for such solution intends to utilize the antiperspirant active in solution, it is preferable not to handle the dry powder and redissolve it, but work with the solution initially. Furthermore, although the Al/Zr/glycinate complexes are more effective than antiperspirant actives that do not contain zirconium, the zirconium compounds utilized are the more expensive component. Where more efficacious forms of Al/Zr glycinate complexes are available such as with the invention product, reducing the quantity of zirconium compound is economically advantageous while at the same time maintaining the efficacious properties of the active.

Throughout this disclosure chromatographic peak profiles are sometimes referred to as "bands." The relationship of "band" to "peak" is as follows: band I=peak 1+2; band II=peak 3; band III=peak 4; band IV=peak 5; etc.

SUMMARY OF THE INVENTION

This invention relates a process for preparing an enhanced antiperspirant active solution having improved stability which comprises blending an enhanced basic aluminum chloride having a peak 4 content of at least 20% (Component A) with a zirconium hydroxychloride neutral amino acid complex (component B) and a conventional basic aluminum chloride (Component C) the order of addition not being critical; wherein at least 10% by weight of the total aluminum being derived from Component A and about 90% to 10% of the aluminum being derived from Component C; thereby forming a stable antiperspirant active solution of enhanced efficacy, the overall concentration of reactants in solution being about 38% to 55% by weight.

This invention also relates to a product made by the foregoing process, said product being an antiperspirant active solution having peak area ratios such that peak 5≧peak 4>peak 1. The product may be dried by conventional drying methods such as spray drying, freeze drying tray drying or ball drying to form a powder.

Other features and advantages of the present invention will become apparent from the following description of the invention, examples, and accompanying drawings.

DESCRIPTION OF THE DRAWINGS

FIG. 3 shows the percent area polymer profile of the composition of this invention FIG. 4 shows viscosity profiles over time of the invention product and conventional product.

As shown in FIGS. 5A and 5B, peak (1+2) was 12% for the invention product and 31% for the conventional product.

DETAILED DESCRIPTION OF THE INVENTION

Figure 1:
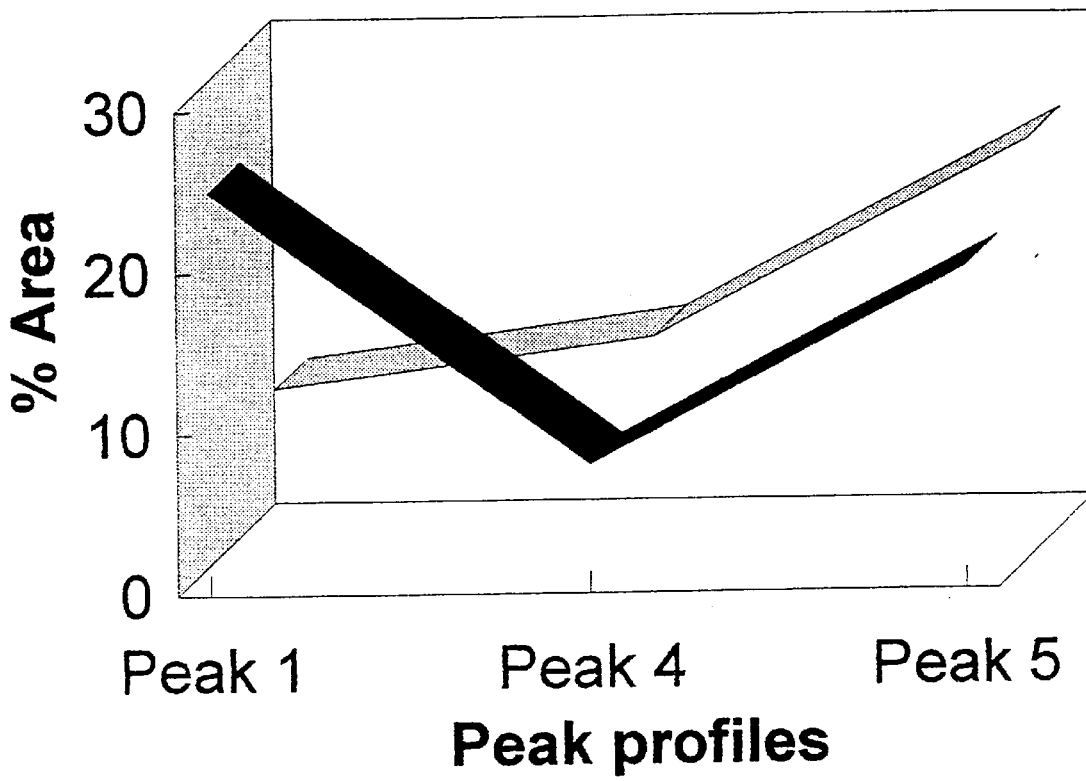
FIG. 1 is a comparison chart of chromatographic peak profiles of the aluminum/zirconium complex antiperspirant active product of the subject invention and of the conventional aluminum/zirconium complex antiperspirant active product.

This invention relates to stable antiperspirant solutions. In particular, the stability of the solutions is characterized by the fact that the solution upon standing at room temperature does not exhibit significant changes in viscosity. Additionally, the peak (1+2) polymer content is low and is quite stable at ambient conditions It has surprisingly been found that polymeric basic aluminum zirconium halide/glycinate complexes having improved antiperspirant activity can be prepared by first preparing a basic aluminum halide having the empirical formula:

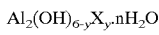

$Al_2(OH)_{6-y}X_y \cdot nH_2O$ wherein y has a numerical value from about 0.7 to about 3, preferably from about 1.0 to about 1.2; X is chlorine, bromine or iodine, preferably chlorine; n is a numeral from about 0.8 to about 4.0, preferably from about 2.2 to about 2.4 and the polymer distribution as characterized by size exclusion chromatogram test is: (a) 100% of the aluminum containing polymers are found in bands II, III and IV, and (b) band III contains at least 25% of the polymers, can be prepared by reacting an aluminum metal with a halogen compound having the formula HX where X is as previously defined, while maintaining the temperature of the reaction mixture at about 50° C. to about 100° C. The aluminum metal is preferably in the form of pellets or powder.

The amount of water used is such as to have the final concentration of the polymer solution, in percent by weight, in the range of about 8% to about 35%, preferably about 8% to about 25%, more preferably about 15% to about 25%, and most preferably from about 17% to about 22% by weight. The reaction temperatures are in the range of 40° to 100° C., preferably in the range of about 95° C. to about 100° C.

The aluminum halohydrate so formed is then combined with a conventional aluminum halohydrate which raises the solids content above 35%. When this aluminum halohydrate solution is promptly reacted with the zirconium compound containing a neutral amino acid such as glycine, the resulting aluminum zirconium halohydrate glycinate solution containing 38–50% solids is surprisingly different than the conventional solution form. The novel product is more efficacious, has polymer stability and is viscosity stable. The peak (1+2) polymers are exceptionally low and the peak (5+6) polymers are exceptionally high. Additionally this polymer arrangement is very stable at ambient conditions for months. The most preferred concentration of this novel product is 40–45% and has desirable applications in aqueous emulsions, and water in oil (w/o) emulsions. An example would be in clear soft gel antiperspirant formulas which are generally w/o systems. A more efficacious active is desirable in these systems because the exterior oil phase reduces the effectiveness level by forming a barrier on the skin surface. The aluminum to zirconium atomic ratio for these compounds are 2.0–8.0:1 and most preferably 3.0–4.0:1. Typically aluminum zirconium tetrachlorohydrex-gly with an atomic ratio of about 3.5:1 is used in such formulas.

The improved activity of the Al/Zr/glycinate complexes of the U.S. Pat. No. 4,871,525 process are attributed to the ratio of peak 4 to peak 3 being about 0.5 to about 1.8.

Conventional basic aluminum chlorides are generally prepared at concentrations of about 50% wt./wt. in water. These conventional salts are stable in solution. However, they lack the degree of efficacy desired in many antiperspirant products. The enhanced zirconium complexes of these salts have improved activity, but limited stability in solution. Furthermore, the manufacture of these salts at low concentrations, e.g. less than 35% results in high production costs.

It has been found that stable low cost solutions high in efficacy can be prepared by reacting an aluminum metal with a halide containing compound, i.e., HCl or an aluminum halide, and subsequently adding a conventional basic aluminum halide.

The term "conventional basic aluminum chloride" is used to distinguish basic aluminum chloride ("BAC") prepared by the direct reaction of aluminum with a chloride containing acid at high concentrations, e.g., 50% by weight, from those products which are described in the art as being enhanced aluminum chlorhydrates. The enhancement refers to improved antiperspirant activity which is generally attributed to characteristics of the BAC polymer as observed from gel permeation chromatography studies.

U.S. Pat. No. 4,359,455 alleges that the enhancement is a result of a high "Band III" peak as shown in the chromatograph of the product U.S. Pat. Nos. 5,358,694 and 5,356,609 disclose a process for preparing enhanced BAC where the enhancement is attributed to a high Band III as well as the elimination of any Band I component from the BAC.

U.S. Pat. No. 4,871,525 prepares an enhanced BAC complex utilizing the methods of the '694 and '609 patent disclosures and subsequently reacting that product with a zirconium compound. The defining characteristic is alleged to be a peak 4 (Band III) to peak 3 (Band II) ratio of about 0.5 to about 1.8. Similarly, U.S. Pat. Nos. 4,775,528 & 5,114,705 attribute the improved properties of the product to a peak 4 to peak 3 ratio of at least 1.5, preferably at least 2.0. U.S. Pat. No. 5,488,347, which is based on the same disclosure as the '528 and '705 patents, further suggests that it is preferred that at least 80% of the product is in the peak 4/3 ratio range as described Immediate spray drying is suggested as a requirement of the prior art in order to maintain the desired characteristics where the solution be spray dried immediately without substantial cooling of the solution.

PCT patent application publication number WO 92/04281 discloses methods for preparing an allegedly efficacious antiperspirant active. The processes disclosed are variants of the processes of the '456 and '525 patents described above. The distinction lies in the use of higher concentration of basic aluminum chloride solutions in preparing the products. It is alleged that efficacy is a result of high Band II and low Band III content of the basic aluminum chloride used to make the Zr/BAC polymer complex While efficacy tests are presented, they are of limited value in determining improvement in efficacy over other types of antiperspirant actives since there is no comparison data, because there is no comparison with similar formulations All that is disclosed is the result achieved with the products of the invention. It is noted that efficacy was determined utilizing spray dried powders in the formulations. Additionally, roll-on formulations will always demonstrate better sweat reduction than aerosol products.

The PCT patent application erroneously states that antiperspirant actives of the prior art having a preponderance of Band III species are made by processes that "generally require high heating temperatures." This is of course incorrect as evidenced by the fact that the PCT process is the same as the '525 process with the concentration being changed, and addition of the zirconium compound at room temperature The '525 patent utilizes the in situ BAC process of U.S. Pat. Nos. 5,358,694 and 5,356,609.

Where the formulation in which the antiperspirant active is to be used requires a water solution of the active, the overall economies are improved from the formulator's stand-point if the active is received in solution form Generally, the prior art suggests that cooling of the solutions results in a loss of efficacy; see for example the disclosure of U.S. Pat. No. 4,871,525. Indeed, if one were to cool the solution prepared according to the '525 patent the peak 4 (Band III)/peak 3 ratio is less than the required 0.5 value as taught by the '525 patent. Similarly, the Band III value is significantly reduced.

The process of this invention utilizes the process of the '525 patent to produce an enhanced BAC. A conventional BAC is then added to the enhanced solution with the subsequent addition of a zirconium compound. The order of addition is not critical Not wishing to be bound by theory, it is believed that the efficaciousness of the product is a result of the high concentration of $Al_{13}$ species in the enhanced BAC. This species leads to a synergistic reaction which rearranges the zirconium compound structure resulting in an efficacious product, notwithstanding the fact that one of the components, the conventional BAC, is known to have a low efficacy compared to enhanced products. Surprisingly, a preferred combination of BAC's is one where more aluminum is contributed by the conventional BAC rather than the enhanced BAC. The enhanced BAC utilized in the practice of this invention should have a Band III component of at least 20% while hot, immediately after preparation thereof. The solution addition can be made either hot or cold. When the enhanced BAC solution is cooled, the Band III component is reduced and the peak 4/peak 3 ratio is less than the 0.5 value required by the '525 patent process. While the solution can be spray dried, it is advantageous to utilize the solution directly when the ultimate product to be formulated requires a water solution of the antiperspirant active, e.g., aqueous base roll-on antiperspirants as well as gels and emulsions (w/o and o/w).

The solutions of this invention have solids content of about 38% to about 55%. In a preferred embodiment, the enhanced BAC utilized to prepare the aluminum zirconium chlorohydrate glycinate complexes of this invention has a peak 4 content of at least 20%. It should be noted that wherever a reference is made to % peak, what is intended is the % area of the peak as compared to the total area of the chromatographic metal containing peaks.

The size exclusion chromatogram test was used to determine polymer distributions, contents and relative retention times of peaks 1, 2, 3, 4, and 5 on the samples of the compositions of this invention and samples of known compositions This test is an analytic technique related to high performance liquid chromatogram (HPLC) In carrying out the tests, a Waters Associates Model 510 pump. a Rheodyne 700 injector, a 410 refractive index detector, and a 730 data module were used for the HPLC instrumentation. Two $\mu$ porasil 125 @ GPC columns 3.9×30 cm (Waters Cat. No. 27477) and a syringe with Luer Lok 0.45 micron prefilters were used in the adsorption.

The directions for carrying out the test are as follows:

In preparing the mobile phase, pipette 16.7 ml. conc. nitric acid into 18.9 liter of distilled water. The diluted nitric acid has a pH of 2.2. Prior to contact with the mobile phase, new columns should first be flushed with isopropanol for about one hour at 0.3 ml/min. since these new columns are packed in 1:1 solution of isopropanol/dichloromethane. New columns should be conditioned with the mobile phase at least three hours prior to sample testing. Turn pump on to 0.8 ml/min., first flushing the reference side of the refractive index cell several minutes, then switching to sample side. Referring to the operator manual, zero in the R.I. detector and set the attenuation of 16×. Also set the 730 data module to the following parameter values:

Minimum area rejection 1000

Minimum peak width rejection 5 seconds

Minimum height rejection 300

Threshold (peak height/peak width rejection ratio) 20

Run/Stop=10 minutes

Sensitivity (Attenuation)=16

Scale factor=48

Sample rate=1

Filter time constant=1

Internal temperature=33° C.

The analytical procedure is as follows:

Pipette 0.2 ml. 12 M hydrochloric acid into a 25 ml volumetric flask containing distilled water, dilute to mark and mix After the detector and columns have reached equilibrium as seen by the stability of the response on parameter 51, set parameter 51 to read 5,000–10,000 by turning the optical zero knob on the detector, being certain that operating temperatures within the room remain constant since the slightest change in the temperature will be sensed by the R.I. detector which will create a base line drift.

Inject a 15 ml. sample of 0.1 N hydrochloric acid standard and observe its retention time (the retention time in this analytical test was found to be 5.70 minutes). Set parameters 81 and 82 to retention time values off 5.40 and 6.00. minutes which will inhibit and resume integration without integrating the hydrochloric acid band itself which contains no aluminum polymers.

Conditioning the Column

The column is conditioned using a 10% w/w solution of Al/Zr tetrachlorhydrex-Gly where the peak 1 area is about 35% to about 45%. To prepare the conditioning solution a 50% w/w solution of Zr/Al tetrachlorhyrate is prepared by heating a 50% w/w solution of conventional aluminum chlorhydrate to about 98° C. and slowing adding a 50% w/w solution of zirconium hydroxychloride having a Zr/Cl mole ratio of 0.7, over several hours with good mixing. The solution is cooled to room temperature, and filtered to form a clear solution. Eight grams of glycine are then added to 100 grams of the filtered solution to form a ZAG. The mixture is then diluted to a concentration of 10% w/w with distilled water. This conditioning solution must be prepared freshly prior to use.

To condition the column it is first flushed with dilute nitric acid (pH=2.2) at a rate of 0.8 ml/min. The column is then injected 40 times with 5 microliters of the 10% ZAG conditioning solution. Then flush the column with nitric acid solution (pH=2.2) and wait one hour. Inject a 1% solution of a standard reference material (monitoring solution). The monitoring solution is a typical production low Zr active, Al/Zr trichlorohydrex-gly. Repeat these steps until the % peak 1 in the monitoring solution is constant.

Let the detector and column stabilize (no more than +1 mv change in the signal of the baseline in 10 minutes) prior to running a sample. Stabilization is achieved by running the mobile phase through the column for at least 30 minutes. The sample to be tested is diluted to 1% w/w with freshly prepared nitric acid mobile phase (pH=2.2), and filtered through a 0.45 micron filter. Inject the sample with a Rheodyne injector (1.5 microliter fixed loop injected).

The chromatogram will show which aluminum containing polymer peaks are presents the retention times of each peak and their calculated percentages.

Calculation:

$$\frac{\% \text{Peak to be}}{\text{determined}} = \frac{\text{(Area Percent of Peak to be dertermined)}}{\text{Total Area Percent of } Al \text{ containing Peaks}}$$

In preparing the antiperspirant active of this invention the order of addition does not appear to be critical. The components utilized are a conventional basic aluminum chlorides, enhanced basic aluminum chlorides and a zirconium hydroxy chloride.

The enhanced basic aluminum chloride ("enhanced ACH") is prepared in situ in the manner described in the '525 patent, and has a peak 4 (Band III) of at least 20%.

The zirconium compound can be prepared by reacting a zirconium basic carbonate (ZBC) with HCl or by reacting the ZBC with a zirconium oxychloride (ZOC) and water. The zirconium compound is then buffered by the addition of glycine.

As stated in U.S. Pat. No. 4,871,525 the preferred concentration of the zirconium hydroxy chloride is about 50–55%. Percent zirconium prior to the amino acid addition should be 20–28% more preferably 22–27%, most preferably 24–26%. When solvent water is limited in the solution, the tendency for the zirconium molecular structure to revert to higher polymer structures is suppressed. This is particularly beneficial after an amino acid such as glycine is added. Although glycination is ideally made at room temperature, the addition can be made at temperatures below 60 deg C. without polymerization effects.

The conventional basic aluminum chloride (BAC) is prepared by reacting aluminum with hydrochloric acid to form a BAC at high concentrations of solution, generally about 50% w/w. These conventional BACs do not contain appreciable amounts of peak 4 and are typically less than 6%.

Preparation of aluminum chlorhydrate

While the aluminum chlorhydrate product of this invention can be defined as having the empirical formula $Al_2(OH)_{6-y}X_y$, where y is 0.7 to 3 and X is chloride, bromine or iodine, it will be understood by those skilled in the art having access to this disclosure, that the aluminum halohydrate of this invention has associated with it both free water and coordinated water. The empirical formula showing this water is $Al_2(OH)_{6-y}X_y \cdot nH_2O$, where y and X are as previously defined and n has a numerical value of about 0.8 to about 4; preferably about 1 to about 3.5; more preferably about 2 to about 3. Approximately 85 wt. % of the water is coordinated water as contrasted with conventional aluminum chlorhydrates which contain about a relative 60% coordinated water.

The process comprises reacting metallic aluminum in the form of pellets, powder, chips or bar with a hydrohalogen acid of the formula HX, where X is chlorine, bromine or iodine. Preferably the acid is HCl.

While the reaction can be carried out at a temperature of about 50° C. to about 100° C., it is preferred that the reaction is carried out at about 80° C. to about 100° C.; more preferably at about 90° C. to about 100° C.; most preferably at about 95° C. to 100° C., e.g., about 96° C. to about 98° C. The reaction is carried out in the absence of reflux conditions. Refluxing can result in reduced formation of the Band III component, and will result in the formation of pre-Band I high molecular weight polymers However, it is within the scope of this invention to utilize a condenser to return water evaporated during the process to the reaction vessel in order to maintain the proper concentration of reactants and product in the reaction mixture.

Successful practice of the invention is best achieved when the quantities of aluminum, water and acid are selected so as to result in an exotherm of at least 5° C. Preferably, about 10° C. to about 20° C. The desired exotherm can be achieved by using a concentration of HCl such that the water/HCl solution formed is at least a 3 wt. % concentration of HCl in the water; preferably about 5 wt. % to about 8 wt. % HCl. It is not necessary to premix the water and HCl in order to commence the reaction. It is preferred that they be added separately As used in the specification and claims with reference to HCl, the concentration indicated means that concentration which a water/HCl solution would have if the quantity of water and acid utilized in the process were pre-mixed, notwithstanding the fact that pre-mixing is neither required nor preferred.

Generally, an excess of aluminum is used in carrying out the reaction process of this invention. This is so since aluminum must always be present throughout the reaction in order for the final product to be formed. However, where the aluminum is in a powdered form the reaction will go to completion using stoichiometric amounts of aluminum and HCl based on the anticipated formula of the products For example, where the desired product is $Al_2(OH)_5Cl$ the HCl/Al ratio is determined based on that formula for aluminum chlorhydrate, and not on the stoichiometric amounts required to form aluminum chloride.

In carrying out the process of this invention the aluminum is preferably in pellet or powder form While chemically pure aluminum can be utilized in the practice of this invention, it is not preferred. The aluminum of choice contains trace amounts of iron or copper. The iron and copper catalyze the HX-aluminum reaction, which results in substantial heat generation, thereby minimizing the amount of heating required to maintain the reaction mixture at the proper temperature. The preferred aluminum is an iron containing aluminum.

Although the concentration of iron in the aluminum can range from about 0.02 to about 0.25 wt. % in the preparation of concentrated solutions of aluminum chlorhydrate of the prior art, in the practice of this invention the iron concentration in the aluminum must be limited to about 0.02 to about 0.15 wt. %. Reactions which use aluminum having iron impurities of greater than 0.15% can result in aluminum salts having iron contents greater than the acceptable limits of the cosmetic trade. The concentration of copper in the aluminum can be about 0.005 to about 0.2 wt. %. Preferably, however, the copper content of the aluminum is about 0.005 to about 0.03 wt. %. It is of course within the scope of this invention to utilize aluminum metal containing both iron and copper.

A critical aspect of the process of this invention is the final concentration of aluminum halohydrate in the reaction mixture which must be maintained at a concentration in percent by weight in the range of about 8% to about 35%, preferably about 8% to about 25%, more preferably about 15% to about 25%, and most preferably from about 17 to about 22% by weight. Above 25 wt. % the amount of peak 4 in the product diminishes where the halogen is chlorine. For example, at a 35% concentration the Band III component is reduced to about 20% for an aluminum chlorhydrate. While the Peak 4 levels will be higher where the halogen is bromine, though a desirable product, aluminum bromohydrate is not the most preferred product.

The process can be most advantageously practiced over the entire 8 to 35 wt. % range. It is preferred, however, that the minimum concentration be at least 15 wt. % Below 15% the solutions of product are cloudy. There appears to be a relationship between the cloudiness of the reaction solution and the development of higher molecular weight species found prior to Band II in the chromatographic distributions When reactions are carried out in solutions having a concentration of less than 15%, the development of cloudiness can be avoided by reducing the reaction temperature and shortening the reaction time. Where the solution concentration is below 15% it is preferred that the reaction temperature is below 90° C. and that the reaction time is less than 24 hours; more preferably the reaction temperature is about 70° C. to about 85° C., e.g., 80° C.

The polymer distribution achieved by the above described process is one of extremely narrow polydispersity, particularly when the final batch concentration of aluminum halohydrates falls within the range of 17%–22% and the metal to halogen atomic ratios are about 1.00:1 to about 2.10:1. Preferably these ratios are about 1.50:1 to about 2.10:1; more preferably about 1.90:1 to about 2.00:1.

The invention product is utilized as a liquid solution. In contrast the prior art enhanced products are generally converted to powdered form to retain the high level of Band III (peak 4) developed in the in situ process.

It will be appreciated by those skilled in the art having access to this disclosure that although the preparation of the BAC is discussed in terms of utilizing HCl as a reactant, it is within the scope of this invention to prepare the BAC by an analogous process as described in U.S. Pat. No. 5,356, 609, incorporated herein by reference, wherein aluminum is reacted with $AlCl_3.6H_2O$ For the purpose of this invention the polymer found in peak 4 by size exclusion chromatography comprises at least 20% of the total aluminum polymer.

Methods of preparation of zirconium hydroxychloride (ZHC) are well known in the art, and do not per se form a part of this invention No benefit is seen in the preparation of ZHC at elevated, refluxing temperatures, and room temperature preparation is preferred In fact, where the process of PCT International Publication No. WO 92/04281 is followed, and the ZHC is prepared by refluxing, utilizing zirconium oxychloride causes the product to gel. As shown in the examples, no gelation occurs with the process of this invention in the absence of reflux. The terms "reflux" or "refluxing" as used in the specifications and claims mean that the reaction mixture is at or above its boiling point.

While conventional aluminum chlorhydrate can be made over a range of concentrations, e.g., 35%–60% w/w in water, generally, the product is prepared commercially at about a 50% concentration as demonstrated in the component C preparation.

Preparation of Component C

Figure 2:
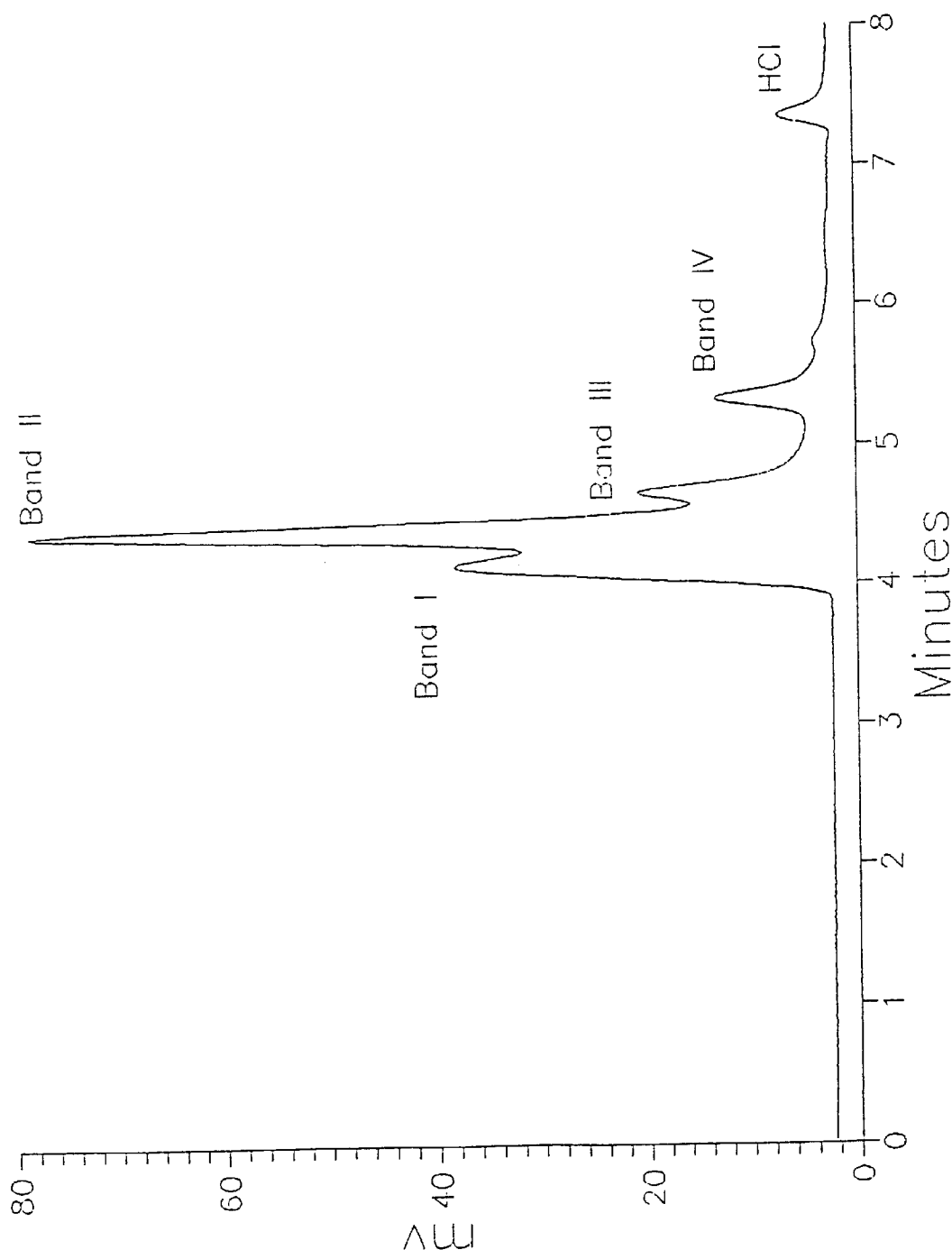
FIG. 2 shows four typical aluminum containing polymer bands for basic aluminum chloride (BAC) with relative retention times calculated with respect to the retention time of hydrochloric acid.

In a glass reaction flask, equipped with a reflux condenser and thermometer, 188 g. of aluminum powder was reacted with 919 grams of deionized water and 392 g. of 20 Baumé hydrochloric acid. The batch was heated to 95° C. until nearly all the aluminum was in solution and the aluminum to chloride atomic ratio was determined by analysis to be 200:1. The resulting 50% solution was filtered and its polymer composition was determined by the size exclusion chromatogram test previously described The chromatogram in FIG. 2 shows four typical aluminum containing polymer bands with relative retention times calculated with respect to the retention time of hydrochloric acid. Table I shows the retention times, relative retention times and the percent of the total aluminum polymers found in each band.

TABLE I

| BAND | RT(Min.) | RRT  | AL POLYMER |
|------|----------|------|------------|
| I    | 3.72     | 0.65 | 39.23      |
| II   | 4.08     | 0.72 | 54.98      |
| III  | 4.38     | 0.77 | 2.95       |
| IV   | 4.89     | 0.86 | 2.85       |

The product was analyzed and found to contain Al=12.5%,l Cl=8.25%, Al:Cl=2:1. The specific gravity of the solution was 1.338.

The last unintegrated band in FIG. 2 is that of hydrochloric acid which exists as free acid to some degree in all basic aluminum chlorides In accordance with the test procedure described in the invention this peak was eluted at 5.7 minutes and it is this retention time that is used as the basis in calculating relative retention times of all other bands The range of relative retention times for purposes of the invention has been defined as shown in Table II.

TABLE II

| Band No. | Relative Retention Time Range |
|----------|-------------------------------|
| Peak 2   | 0.62–0.70                     |
| Peak 3   | 0.71–0.75                     |
| Peak 4   | 0.76–0.82                     |
| Peak 5   | 0.83–0.97                     |

The 50% solution obtained in this example is a standard product in the industry and can be marketed as such or further processed to a basic aluminum chloride powder through common techniques such as spray drying, vacuum drying etc. This BAC is referred to as "conventional basic aluminum chloride". It can be prepared at concentrations of 35% or greater. Typically conventional BAC will have a Band I component of at least 25%; more typically at least 30%, while the Band III component of the polymer will generally be less than 6%.

When high basic forms of concentrated basic aluminum chlorides are used i.e., where the aluminum to chloride ratio is about 1.9:1 and the concentration is about 50%, if the solution is used within 72 hours after preparation, the Band I values will be slightly lower than aged solutions. These freshly prepared solutions are preferred for use in making the invention product Preparation of Component A (A) A 20% solution of enhanced aluminum chlorohydrate was prepared by reacting 2.4 kg. of granulated aluminum, 12.5 kg. of distilled $H_2O$ and 4.25 kg. 20 Baumé hydrochloric acid in a 50 liter reaction flask. During the exotherm of the reaction an additional 21.47 kg. of distilled $H_2O$ was charged. The temperature of the batch was maintained at 98° C. through the oxidation reduction reaction for 72 hours. A sample was taken, filtered and tested for polymer composition using the size exclusion chromatography method previously described. The sample was also analyzed for percent aluminum, percent chloride and aluminum/chloride atomic ratio The analysis and HPLC results for the 20% aluminum chlorhydrate solution are shown below.

TABLE III

| 20% Solution | |
|---|---|
| Al/Cl ratio | 1.94:1 |
| % Aluminum | 5.00 |

TABLE III-continued

| 20% Solution | |
|---|---|
| % Chloride | 3.38 |
| % Peak 2   | 0.0  |
| % Peak 3   | 59.1 |
| % Peak 4   | 39.6 |
| % Peak 5   | 1.3  |

While component A can be prepared at concentrations of about 8% to 35% (w/w) it will typically be prepared at concentrations of about 15% to about 25%, e.g. about 17% to about 22%. In preparing the composition of this invention the enhanced BAC prepared in situ should be used fresh, preferably within 72 hours of its manufacture. If time constricts prevent such immediate use, the product should be dried, and the powder reconstituted in solution for use at an appropriate time. Any rapid drying technique such as spray drying or freeze drying can be used.

Preparation of Component B

In accordance with the invention there is provided a process for preparing an Al/Zr complex from a zirconium hydroxychloride having the empirical formula:

$$ZrO(OH)_xCl_{2-x},$$

wherein x has a numerical value of 0–1.5. The metal to chloride atomic ratio of the zirconium hydroxychloride is preferably about 0.60 to 0.90:1. Where the Zr/Cl atomic ratio is about 0.90:1, the final product is an aluminum zirconium trichlorohydrex-gly. Where the Zr/Cl ratio is 0.60:1 the final product is an aluminum zirconium tetrachlorohydrex-gly. In the practice of this invention a solution of the zirconium hydroxychloride is prepared and reacted with a solution of Components A and C.

The amount of water used in preparing the zirconyl hydroxychloride solution (Component B) is such that the percentage by weight of hydroxychloride in solution is about 20 to about 55%. In one embodiment of the invention the concentration of hydroxychloride is about 50%–55% by weight. By using the higher concentration range, the rate of complexing between the amino acid and the basic zirconium chloride is greatly retarded, thus allowing for a lower form of complex in the final product.

The zirconium hydroxy chloride may be heated and air sparged to remove the carbon dioxide formed during the reaction. Heating should not raise the temperature of the reaction mixture above 75° C. Preferably the ZHC is formed at about 50° C. The concentration of ZHC in solution prior to glycination can be about 20% to 55%, e.g. 50%.

The atomic ratio of Zr/Cl can be about 0.6:1 to about 1.1:1. Where acidity comes primarily from the BAC the Zr/Cl ratio can be about 1:1. In the case basic aluminum chlorides such as aluminum zirconium tetrachlorohydrex-gly and aluminum zirconium octachlorohydrex-gly the Zr/Cl ratio can be about 0.6 to about 0.8:1.

A neutral amino acid, such as glycine can be added to the solution to form a zirconium hydroxy chloride amino acid complex The atomic ratio of amino acid to zirconium is in the range of 0.5:1 to about 1.31, typically about 0.7:1 to about 1.1:1, e.g. 0.8:1 to about 1.0:1. The glycine should be added at a temperature below 60° C.

Component A can then be added to Component C. Component A comprises a solution containing about 8 to about 35 wt. % aluminum halohydrate prepared by the afore-described reaction process having a peak 4 of at least 20%.

Upon mixing of the three solutions A,B, and C there is formed an efficacious, polymer stable and viscosity stable aluminum-zirconium hydroxy halide-amino acid complex of the empirical formula:

$$(Al_2(OH)_{6-y}X_y)_a(ZrO(OH)XCl_{2-x})_b \text{neutral amino acid}$$

wherein x has a numerical value of about 0–1.5, X is chlorine, bromine or iodine, and y has a numerical value of about 0.7 to about 3.0. The values of a and b are selected so that the aluminum/zirconium atomic ratio is preferably about 2.0 to about 8.0. The amino acid to zirconium weight ratio is preferably about 0.4 to about 1.5:1.

In the practice of this invention the proportions of Components A and C are such that about 30% to about 80% of the aluminum is derived from component C. In one embodiment of the invention about 10% to about 90% of the aluminum is derived from Component C; typically about 40% to about 75% of the aluminum is derived from Component C. The solution comprising the blend of Components A, B and C has a solid concentration of about 40 to about 55%, e.g. 40 to about 45%. At least 10% of the total aluminum must be derived from the enhanced BAC (Component A); typically 20% to 40%, e.g. 33%.

The following preparations of the components (A-1, A-2, C-1, C-2, B-1, B-2) were made and utilized in the invention product preparations described in examples 1–6.

Example 7 compares the peak (1+2) content of a conventional aluminum zirconium chlorohydrate glycinate to the invention product.

Example 8 compares the peak (1+2) content of the conventional and invention products that were extracted from clear gel antiperspirant formulations.

Component Preparations

A-1) Enhanced Aluminum Chlorohydrate Solution

To a 4 l resin flask, equipped with a water cooled condensor is charged 416 g of granulated aluminum and 3,027 g of Di-water. 443 g of 32.4% hydrochloric acid was incrementally charged over one hour to allow for a moderate exothermic reaction to take place. The contents were maintained at a reaction temperature of 95 deg C. for 46 hours until the aluminum chloride atomic ratio of the solution was determined by assay to be 1.96:1.

The resulting 21% enhanced aluminum chlorohydrate solution was filtered from the excess aluminum and maintained at 95 deg C. for use in subsequent sample preparations of this invention.

A-2) Enhanced Aluminum Chlorohydrate Powder

A portion of the 95 deg C. solution from A-1 was spray dried in a laboratory spray dryer at 230 deg C. inlet and 100 deg C. outlet. The powder was analyzed and found to contain 25.5% aluminum and 17.0% chloride. A polymer analysis was performed according to the procedure disclosed in U.S. Pat. No. 5,358,694 and was found to contain 45.2% Band III (peak 4) and 0% Band I (peak 1+2). This powder was used in subsequent sample preparations of this invention.

C-1) Conventional aluminum Chlorohydrate Solution

To a 4 liter resin flask equipped with a water cooled condensor was charged 705 g of granulated aluminum metal and 2,500 g of Di-water.

1,048 g of 32.4% hydrochloric acid was incrementally charged over 1 hour to allow for a moderate exothermic reaction. The temperature was maintained at 95 deg C. for 60 hours until the aluminum to chloride atomic ratio of the solution was determined by assay to be 1.93–1. The resulting 50% aluminum chlorohydrate solution was removed from the excess aluminum, filtered and used within a 24 hour period to prepare subsequent samples of this invention.

C-2) Conventional Aluminum Chlorohydrate Powder

A portion of the solution of A-3 was spray dried to a powder using a laboratory spray dryer with an inlet temperature of 230 deg C. and an outlet temperature of 82 deg C. The powder was analyzed and found to contain 24.8% aluminum and 16.8% chloride. A polymer analysis was performed according to the procedure disclosed in U.S. Pat. No. 5,358,694 and found to contained a Band I (peak 1+2) of 21% and a Band III (peak 4) of 5%. The powder was used to prepare subsequent samples of this invention.

B-2) Zirconium Hydroxy Chloride Glycinate Solution (Low Basic)

A concentrated low basic solution of zirconium hydroxy chloride glycinate as prepared as follows:

2.64 Kg of zirconium oxychloride crystal and 0.4 Kg of Di-water was charged to a 4 liter resin flask. The contents were heated to 55 deg C. and 1.03 Kg of basic zirconium carbonate was charged incrementally to control frothing during de-carbonation. The contents were held at 55 deg for 30 minutes to yield a clear solution which was cooled to 25 deg C. The solution was analyzed and found to contain 25.1% zirconium and a zirconium to chloride atomic ratio of 0.68:1. 0.85 Kg of Glycine was charged at 25 deg C. An analysis showed that the solution had 20.6% zirconium and a glycine to zirconium weight ratio of 0.87:1. This solution was used in subsequent sample preparations of this invention.

B-2) Zirconium Hydroxy Chloride Glycinate Solution (High Basic)

A concentrated high basic solution of zirconium hydroxy chloride glycinate was prepared as 2.43 Kg of zirconium basic carbonate was charged to a 4 liter resin flask. 0.742 Kg of 37% hydrochloric acid was incrementally charged over one hour to control frothing during de-carbonation The contents were heated to 65 deg C. for 30 minutes to yield a clear solution which was cooled to 25 deg C. The solution was analyzed and found to contain 24.0% zirconium and a zirconium to chloride atomic ratio of 0.99:1. 0.6 Kg of glycine was charged and dissolved at 25 deg C. An analysis showed that the solution had 20.0% zirconium and a glycine to zirconium weight ratio of 0.85:1. This solution was used to prepare subsequent samples of this invention.

TABLE IV

| | Raw Material Component Analysis | | | | | | |
|---|---|---|---|---|---|---|---|
| Component | Temp deg C. | % aluminum | % zirconium | % chloride | % glycine | % Band I | % Band III |
| A-1 | 95 deg C. | 5.24 | | 3.51 | | 0.0 | 46.5 |
| A-2 | Ambient | 25.5 | | 17.0 | | 0.0 | 44.2 |
| C-1 | Ambient | 12.3 | | 8.35 | | 18.0 | 5.2 |
| C-2 | Ambient | 24.8 | | 16.8 | | 21.8 | 4.8 |

TABLE IV-continued

Raw Material Component Analysis

| Component | Temp deg C. | % aluminum | % zirconium | % chloride | % glycine | % Band I | % Band III |
|---|---|---|---|---|---|---|---|
| B-1 | Ambient | | 20.6 | 11.5 | 17.9 | | |
| B-2 | Ambient | | 20.0 | 7.7 | 17.0 | | |

EXAMPLE 1

300 g of enhanced aluminum chlorohydrate solution (A-1) and 80 g of deionized water were charged to a 1 liter beaker. Immediately, 120 g of conventional aluminum chlorohydrate powder (C-2) was charged with stirring and dissolved. The solution was quickly cooled to 40 deg C. over a 10 minute period and 210 g of zirconium hydroxy chloride glycinate solution (B-1) was immediately charged. The resulting 43% solution had a temperature of 30 deg C. A sample was analyzed and found to contain an aluminum:zirconium atomic ratio of 3.65:1 and a metal-chloride ratio of 1.38:1. The material was allowed to age at 25 deg C. for 90 days. A polymer analysis was performed according to the chromatographic procedure described in this invention. The results were as follows:

TABLE V

| Day No. | % Peak (1 + 2) | % Peak (4) | % Peak (5 + 6) |
|---|---|---|---|
| Initial | 12.5 | 20.0 | 17.5 |
| 5 | 9.5 | 15.2 | 23.6 |
| 20 | 8.6 | 13.2 | 25.2 |
| 60 | 11.9 | 15.0 | 22.2 |
| 90 | 12.5 | 14.0 | 21.9 |

FIG. 3 shows the percent area polymer profile of this experiment. Typically after three days the polymer profile reverts from a peak area order of predominance of peak 4>peak 5>peak 1 to peak 5>peak 4>peak 1. The invention product was polymer and viscosity stable after 90 days.

EXAMPLE 2

51 g of deionized water was charged to a 250 ml beaker and heated to 65 deg C. Heating was discontinued and 15 g of enhanced aluminum chlorohydrate powder (A-2) and 59 g of conventional aluminum chlorohydrate solution (C-1) were charged with mixing to quickly dissolve the powder. The solution was immediately cooled to 25 deg C. in an ice bath and 52 g of zirconium hydroxy chloride glycinate (B-1) was immediately charged with mixing.

The final solution when analyzed, contained 6.29% aluminum, 6.10% zirconium, 7.65% chloride and 5.14% glycine. A polymer analysis was performed according to the chromatographic procedure described in this invention and the following results were obtained:

TABLE VI

| Day No. | % Peak (1 + 2) | % Peak (4) | % Peak (5 + 6) |
|---|---|---|---|
| Initial | 14.5 | 18.8 | 17.9 |
| 5 | 8.0 | 12.9 | 25.9 |
| 30 | 7.8 | 12.2 | 25.4 |

EXAMPLE 3

59 g of conventional aluminum chlorohydrate solution (C-1) and 45 g of deionized water were charged to a 250 ml beaker With stirring 15 g of enhanced aluminum chlorohydrate powder (A-2) and 6 g of 32.4% hydrochloric acid were charged. While the powder was dissolving, 54 g of zirconium hydroxy chloride glycinate (B-2) was charged. The resulting 43% solution of the aluminum zirconium chlorohydrate glycinate complex was analyzed for polymer distribution according to the chromatographic procedure described in this invention. The following results were obtained:

TABLE VII

| Day No. | % Peak (1 + 2) | % Peak (4) | % Peak (5 + 6) |
|---|---|---|---|
| Initial | 17.7 | 17.80 | 15.6 |
| 5 | 9.2 | 15.6 | 21.7 |
| 30 | 11.9 | 12.6 | 23.2 |

EXAMPLE 4

150 g of enhanced aluminum chlorohydrate solution, (A-1) was charged to a 250 ml beaker containing 30 g of conventional aluminum chlorohydrate powder (C-2). The powder was dissolved with stirring while simultaneously being cooled in an ice bath to 25 deg C. over a 5 minute period 75 g of zirconium hydroxy chloride solution (B-1) was immediately charged and mixed. After 3 days a polymer analysis was performed according to the chromatographic procedure described in this invention. Peak (1+2) was 6.5%, peak 4 was 16.0% and peak (5+6) was 26.3%

EXAMPLE 5

This experiment was carried in the same manner as example 2 except that 51 g of a 50-50 weight mixture of propylene glycol and water was used in place of the 51 g of water.

EXAMPLE 6

This experiment was carried out in the same manner as example 2 except that 51 g of a 50-50 weight mixture of dipropylene glycol and water was used in place of the 51 g of water.

EXAMPLE 7

A conventional aluminum zirconium chlorohydrate glycinate compound equal to the concentration and chemical identity of the invention product of example 4 was also prepared. The difference in the method of preparation was that the conventional product was made from component C type material and component B-1 that was refluxed. The viscosity measurements were conducted after 30,60,90 days at an oven storage temperature of 45 deg C. for both samples.

The viscosity profiles are shown in FIG. 4. After 90 days, viscosity of the invention product was 17.8 cps while the conventional product gelled.

EXAMPLE 8

The invention product of example 2 was formulated into a clear gel antiperspirant containing dimethicone copolyol as the gel agent, propylene glycol, cyclomethicone, and water.

Figure 5A:
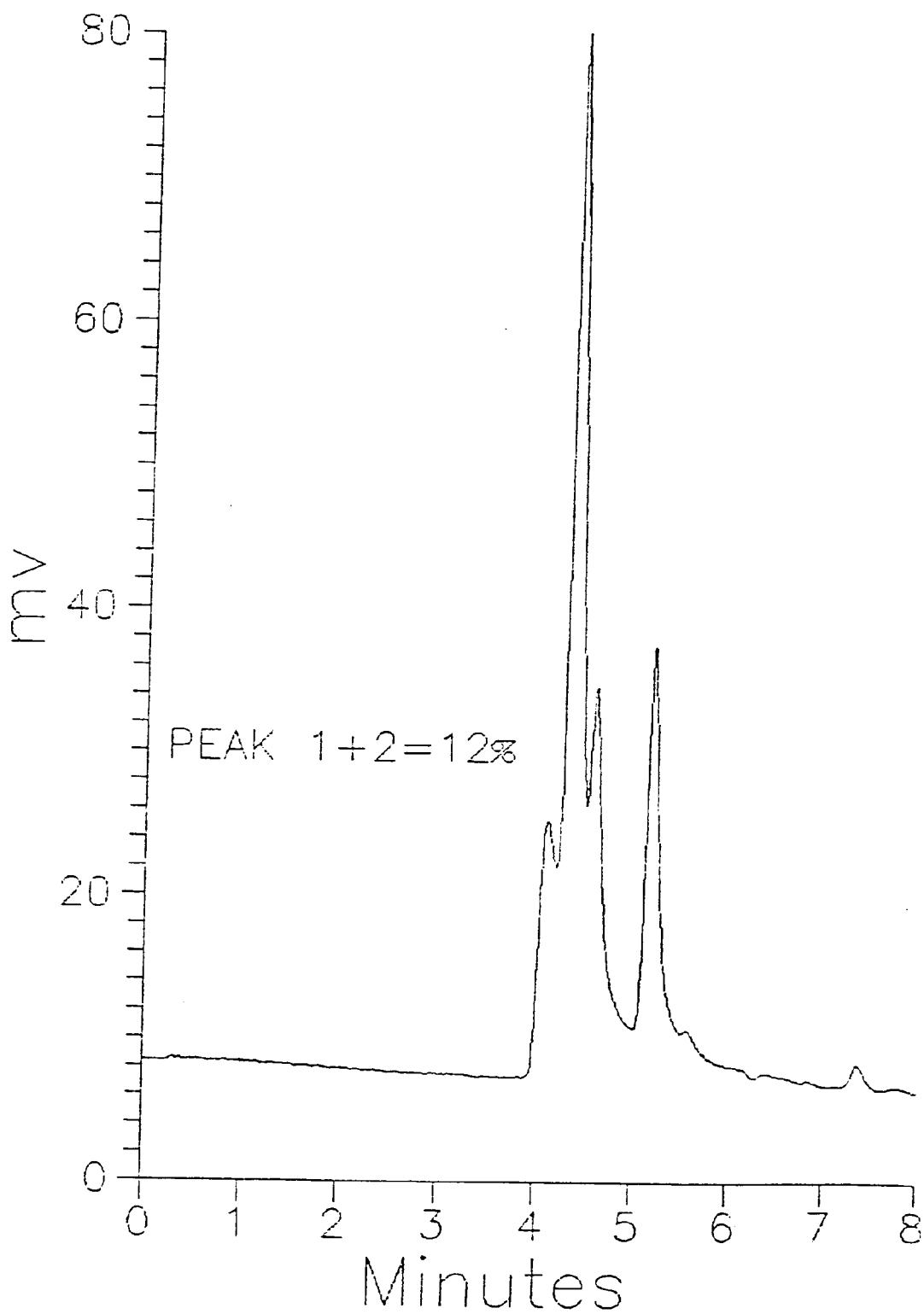
FIG. 5A shows the polymer distribution of the invention product after 30 days of storage in a formulation.
Figure 5B:
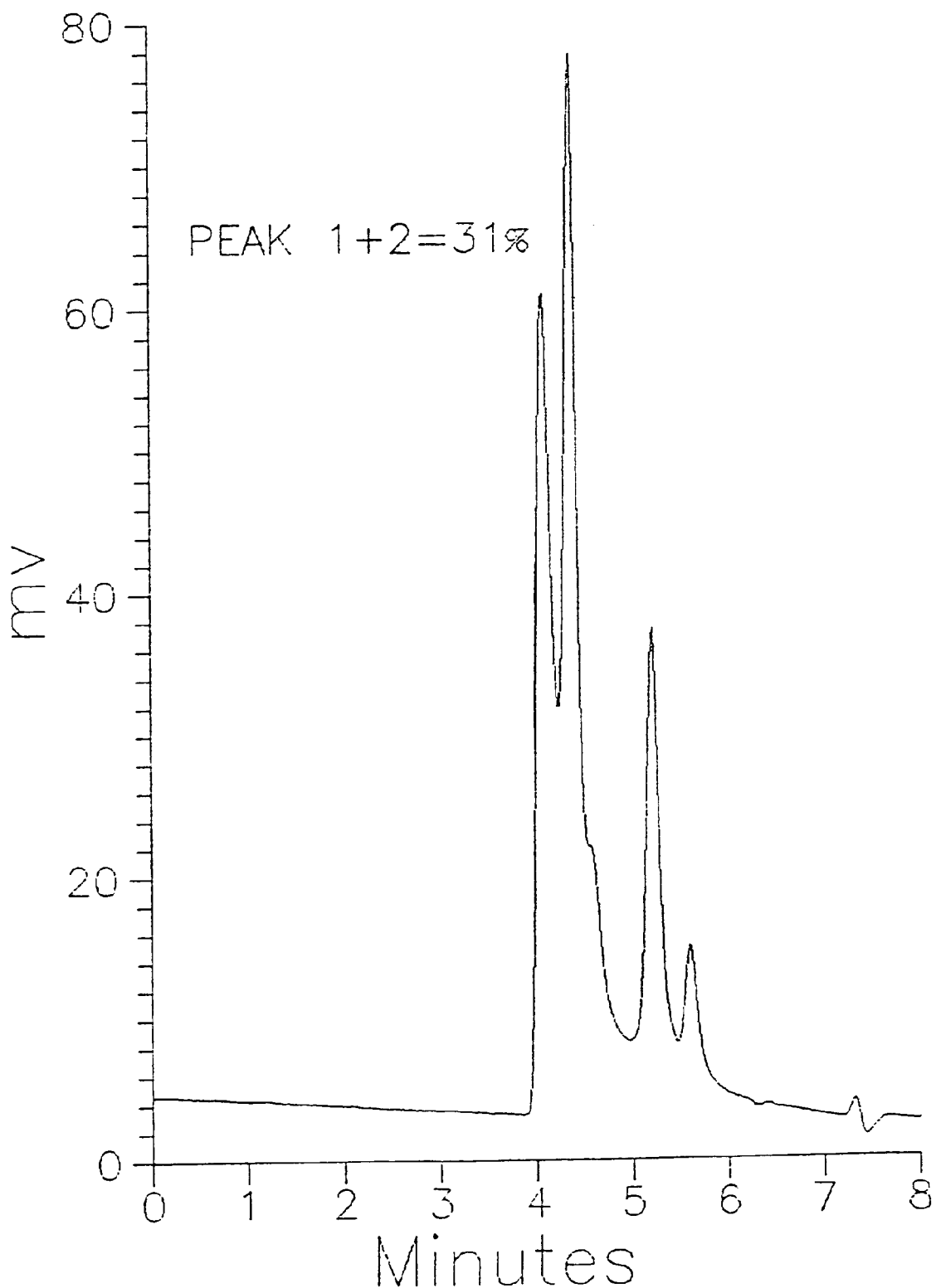
FIG. 5B shows the polymer distribution of the conventional aluminum zirconium chlorohydrate glycinate after 30 days of storage in a formulation.

After 30 days the active was extracted and analyzed for polymer distribution. A conventional aluminum zirconium chlorohydrate glycinate active was extracted from a commercial antiperspirant gel product of the same composition. A polymer analysis was made on this extracted active product which was compared to the extracted invention active product. As shown in FIGS. 5A and 5B, peak (1+2) was 12% for the invention product and 31% for the conventional product.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

EXAMPLE 9

A 125 kg batch of an aluminum zirconium chlorohydrate glycinate complex was prepared in pilot equipment using the method described in Example 2. The raw material components comprising the enhanced aluminum chlorohydrate powder, the conventional aluminum chlorohydrate solution, and the concentrated zirconium hydroxy chloride glycinate solution (B-1 type) were all made on a commercial scale and the following portions were drawn for use in this preparation:

TABLE VIII

| Component | amount kg | % aluminum | % zirconium | % chloride | % glycine |
|---|---|---|---|---|---|
| enhanced aluminum chlorohydrate powder | 11.0 | 25.8 | | 17.2 | |
| conventional aluminum chlorohydrate solution | 42.5 | 12.2 | | 8.3 | |
| zirconium hydroxy chloride | 38.0 | | 20.5 | 11.5 | 17.4 |
| water | 33.5 | | | | |

A polymer analysis was performed on the 56 day after manufacture according to the chromatographic procedure described in this invention. The peak area order of predominance was peak 5>peak 4>peak 1.

A sample of the invention active was formulated into a water in oil clear gel antiperspirant containing cyclomethicone, dimethicone, dimethicone copolyol, dipropylene glycol and water. A control formula of the same composition was made using a competitive antiperspirant active of the same stoichiometry. A five day sweat reduction study was performed on a panel of 60 male subjects with sweat collections taken at 1 hour after the $2^{nd}$ day, 12 hours after the $4^{th}$ day and 24 hours after the $5^{th}$ days. The geometric means were calculated at the 95% confidence level. The antiperspirant gel containing the invention active outperformed the control as indicated in Table IX.

TABLE IX

Comparison of Conventional Active vs. Untreated and Invention Active vs. Untreated

| | % Reduction ± 95% Confidence Interval | |
|---|---|---|
| Collection | Conventional Active | Invention Active |
| Appl. 2 - 1 Hr. | 37.07 ± 14.96 | 41.24 ± 14.41 |
| Appl. 3 - 12 Hr. | 36.62 ± 17.99 | 46.09 ± 14.40 |
| Appl. 4 - 24 Hr. | 19.86 ± 18.79 | 35.89 ± 14.31 |

The test results indicated that the Invention Active exhibited significant efficacy at each time point. The Conventional Active did not exhibit significant efficacy at any time.

Figure 6A:
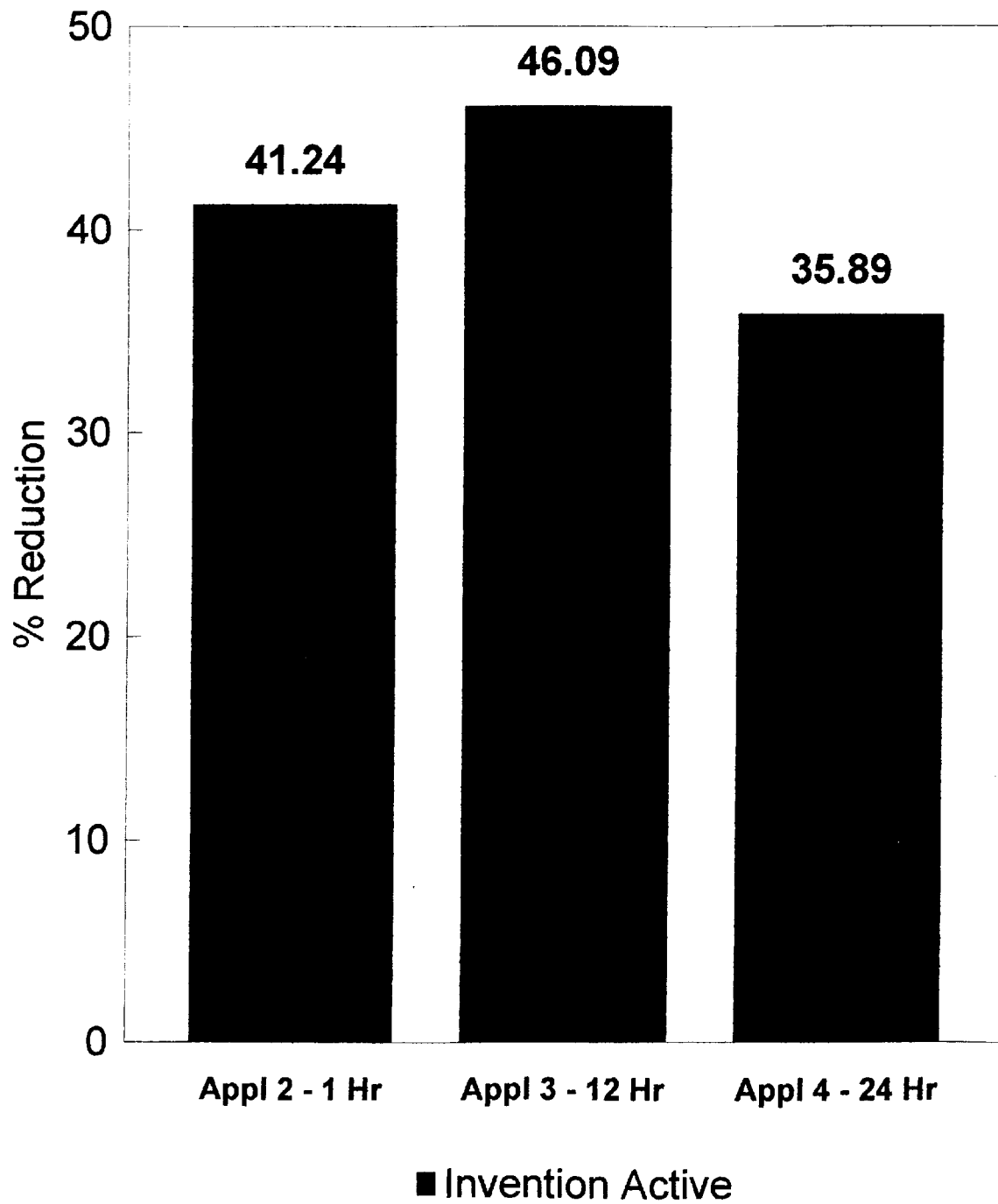
FIG. 6A shows the comparison of conventional active vs. untreated.
Figure 6B:
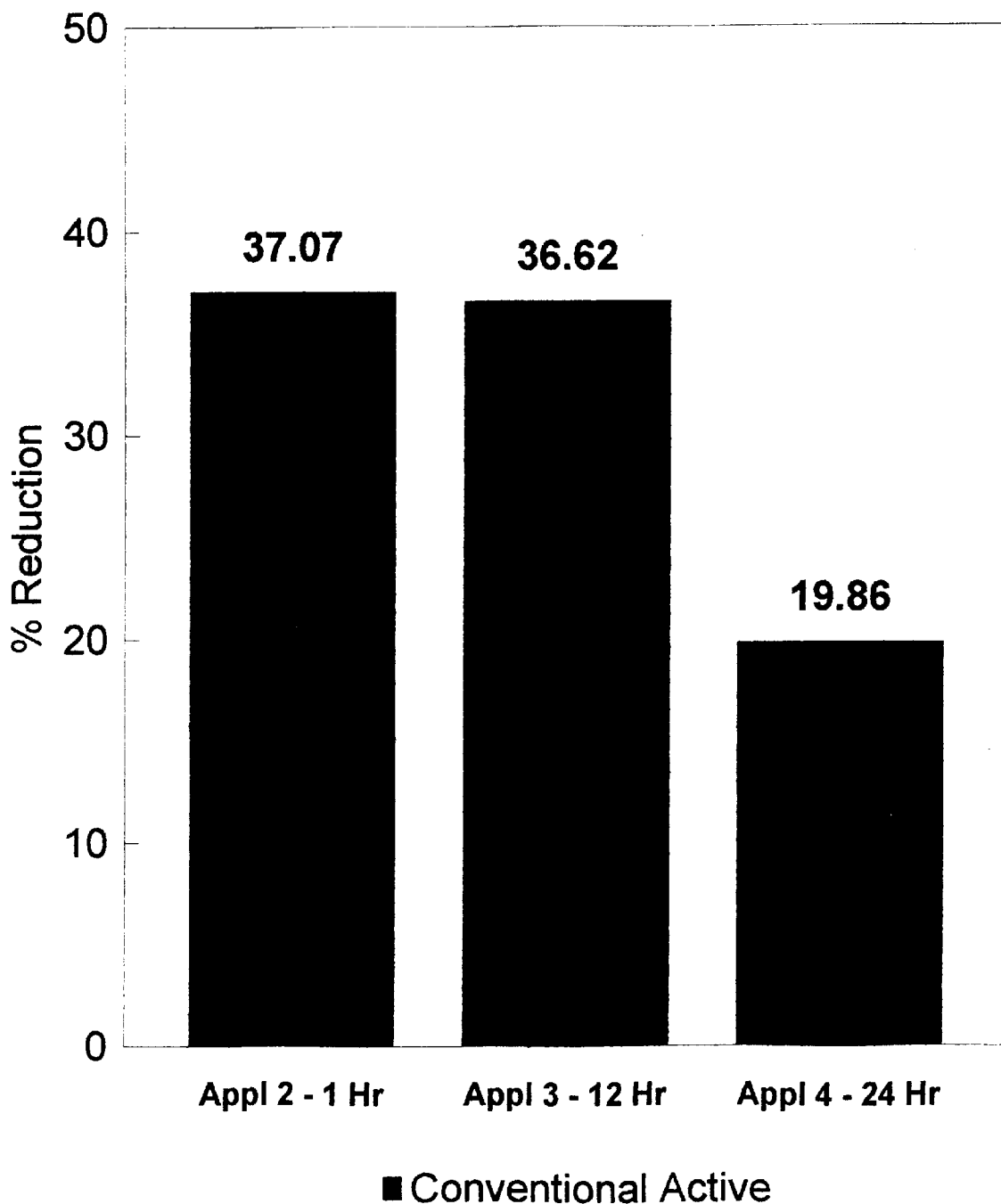
FIG. 6B shows the comparison of invention product active vs. untreated

FIGS. 6A and 6B show the estimates of percent reduction in sweat demonstrated by the Conventional Active and the Invention Active in block graph format.

What is claimed is:

1. A process for preparing an enhanced antiperspirant active solution having improved stability which comprises blending an enhanced basic aluminum chloride antiperspirant active having a peak 4 content of at least 20% (Component A) with a zirconium hydroxychloride neutral amino acid complex (Component B) and a conventional basic aluminum chloride (Component C), the order of addition not being critical; wherein at least 10% by weight of the total aluminum being derived from Component A and about 90% to 10% of the aluminum being derived from Component C; thereby forming a stable antiperspirant active solution of enhanced efficacy, the overall concentration of reactants in solution being about 38% to 55% by weight.

2. The process according to claim 1, wherein about 25% to about 75% of the aluminum in the solution is derived from Component C.

3. The process according to claim 1, wherein the concentration of reactants in solution is about 38% to about 45%.

4. The process according to claim 1, wherein the zirconium hydroxychloride is prepared by reacting a zirconium oxychloride with a basic zirconium carbonate in the absence of reflux conditions at a reaction temperature of less than 75° C.

5. The process according to claim 4, wherein the preparation of zirconium hydroxychloride is facilitated by air sparging to aid in the removal of any $CO_2$ formed thereby increasing the reaction rate.

6. The process according to claim 4, wherein the reaction temperature is about 40° C. to about 50° C.

7. The process according to claim 1, wherein the Al/Cl atomic ratio of the enhanced basic aluminum chloride (Component A) is about 1.85/1 to about 2.1/1.

8. The process according to claim 1, wherein the Al/Cl atomic ratio of the enhanced basic aluminum chloride (Component A) is about 1.90/1 to about 1.98:1.

9. The process according to claim 1, wherein the Zr/Cl atomic ratio in the zirconium hydroxychloride is about 0.6/1 to about 1/1.

10. The process according to claim 9, wherein the Zr/Cl atomic ratio is about 0.65/1.

11. The process according to claim 9, wherein the Zr/Cl atomic ratio is about 0.83/1.

12. The process according to claim 1, wherein the solution comprises a glycol.

13. The process according to claim 12, wherein the glycol is propylene glycol or dipropylene glycol.

14. The process according to claim 11 wherein the neutral amino acid is glycine.

15. The product prepared according to the process of claim 1.

16. A powdered enhanced antiperspirant active prepared by drying the product of claim 1.

17. The powdered enhanced antiperspirant active of claim 16, wherein the drying is spray drying, freeze drying, tray drying or ball drying.

18. An antiperspirant active solution having peak area ratios such that peak 5>peak 4>peak 1.

19. A process for preparing an enhanced antiperspirant active solution which comprises:

(a) preparing an enhanced aluminum hydroxyhalide antiperspirant active solution having a Peak 4 component of at least 20%, and a solids concentration of about 8% to about 35% by weight by diluting a conventional basic aluminum halide to a concentration of about 8% to about 35%, heating the diluted solution at a temperature of about 40° C. to about 100° C. for about 1 to about 48 hours to form an antiperspirant active having a Peak 4 component of at least 20% (Component A);

(b) preparing a zirconium hydroxy-halide neutral amino acid complex by reacting a zirconium oxyhalide, zirconium carbonate and a neutral amino acid in water in the absence of reflux conditions at a reaction temperature of less than 75° C. (Component B);

(c) mixing component A with a conventional basic aluminum halide solution (Component C) having a solids concentration of about 40% to about 50%; and (d) combining the mixture of Component A and Component C with Component B such that the combination at no point in time exceeds about 60° C., and is cooled to about 25° C. within 24 hours.

20. The process of claim 19, wherein the combination of Component A, Component C, and Component B at no point in time exceeds about 35° C., and is cooled to about 25° C. within 8 hours.

21. The process of claim 19 wherein the halide is chlorine and the neutral amino acid is glycine.

22. A process for preparing an enhanced antiperspirant active solution which comprises:

(a) preparing an enhanced aluminum hydroxyhalide antiperspirant active solution having a Peak 4 component of at least 20%, and a solids concentration of about 8% to about 35% by weight by reacting aluminum metal with an halogen containing acid having the formula HX wherein X is chlorine, bromine or iodine in water at a temperature of about 50° C. to about 100° C., the concentration of the product in solution being about 8 to about 25% by weight of the solution, and the polymer distribution of the product formed as characterized by size exclusion chromatography is 100% of the polymers are found in Bands II, III and IV, with no part of the product found in Band I, and Band II contains at least 25% of the polymer (Component A);

(b) preparing a zirconium hydroxyhalide neutral amino acid complex by reacting a zirconium oxyhalide, zirconium carbonate and a neutral amino acid in water in the absence of reflux conditions at a reaction temperature of less than 75° C.;

(c) mixing component A with a conventional basic aluminum halide solution (Component C) having a solids concentration of about 40% to about 50%; and (d) combining the mixture of Component A and Component C with Component B such that the combination at no point in time exceeds about 60° C., and is cooled to about 25° C. within 24 hours.

23. The process of claim 22, wherein the combination of Component A, Component C, and Component B at no point in time exceeds about 35° C., and is cooled to about 25° C. within 8 hours.

24. The process of claim 22, wherein the halide is chlorine and the neutral amino acid is glycine.

25. The process of claim 22, further comprising a step of drying the solution to form a powder.

26. The product prepared according to the process of claim 25.

* * * * *